United States Patent [19]
Scott

[11] 3,969,218
[45] July 13, 1976

[54] ELUTION ELECTROPHORESIS

[75] Inventor: Charles D. Scott, Oak Ridge, Tenn.

[73] Assignee: The United States of America as represented by the United States Energy Research and Development Administration, Washington, D.C.

[22] Filed: Feb. 11, 1975

[21] Appl. No.: 548,941

[52] U.S. Cl. .................. 204/299 R; 204/180 R; 204/180 G
[51] Int. Cl.² .................. G01N 27/26; G01N 27/28
[58] Field of Search ............ 204/180 R, 180 G, 299

[56] References Cited
UNITED STATES PATENTS

| | | | |
|---|---|---|---|
| 2,566,308 | 9/1951 | Brewer | 204/180 R |
| 3,290,240 | 12/1966 | Neren | 204/299 |
| 3,346,479 | 10/1967 | Natelson | 204/299 X |
| 3,649,498 | 3/1972 | Pretorius et al. | 204/180 G |
| 3,704,217 | 11/1972 | Nerenberg | 204/180 G |

*Primary Examiner*—John H. Mack
*Assistant Examiner*—A. C. Prescott
*Attorney, Agent, or Firm*—Dean E. Carlson; David S. Zachry; John B. Hardaway, III

[57] ABSTRACT

Colloids and macromolecules are separated by simultaneously carrying out elution and electrophoretic separation processes.

3 Claims, 3 Drawing Figures

ELUTION ELECTROPHORESIS

BACKGROUND OF THE INVENTION

This invention was made in the course of, or under, a contract with the United States Atomic Energy Commission. It relates generally to the art of particle and molecular separations.

Various methods and apparatus have been used in the prior art for separating macromolecules and colloids. One prior art method is elution chromatography. This technique is alternately referred to as gel chromatography, gel filtration or gel permeation chromatography. Such a method generally comprises placing a sample within a column packed with a continuous or particulate medium. An eluent is then passed through the column to carry individual constituents through the column at differing rates so as to effect a separation of the particles or molecules passing through the eluent. Prior to introducing the sample, the gel with which the column is packed is normally swollen by soaking with eluent. The swollen gel is felt to act somewhat like a filter to the solutes and suspended molecules within the eluent. Various media are used as a gel in such separations. Among the materials utilized as a gel are dextran cross-linked with epichlorohydrin, copolymers of acrylamide and methylene bis acrylamide, polystyrene cross-linked with divinylbenzene, galactose residues with 1, 3 glycosidic linkages, porous glass beads, and chlorobutyl rubber. One problem with gel chromatography is that the process is slow and the degree of resolution leaves something to be desired.

Another prior art separation technique is electrophoresis. Electrophoresis is a general method for separating proteins and other macromolecular materials. Electrophoresis in cast polyacrylamide gels is probably the highest resolution technique available for the analytical separation of macromolecular mixtures such as serum. In this technique the sample is placed on a gel containing an aqueous buffer. A potential diffence is imposed across the gel which causes one end of the gel to be electrolytically positive relative to the other. The macromolecules in the sample also have a charge, and under the influence of the potential difference across the gel these macromolecules move toward the end that has a charge opposite to their own charge. The actual separation of the macromolecules in the sample depends upon the different macromolecules in the sample moving at different rates because of differing charges and sizes. The particular macromolecules separate into bands under the influence of the electric field. After being chemically fixed, the zones are stained for purposes of identification and quantification. The relative concentration of each macromolecule is then determined by photometric scanning using a densitometer. Recovery of the separated species in the inert gel packing can be accomplished by selective sectioning of the gel after removal of the packing from the container. Another recovery technique involves aqueous elution of the packing which is left intact. This type of technique lends itself to simpler detection and recovery of specific fractions in solution.

Resistive heating is a problem of electrophoretic separations which has limited current throughput. Another problem which limits current has been the generation of bubbles at the electrodes resulting from the electrolysis of water.

SUMMARY OF THE INVENTION

It is thus an object of this invention to provide a new process for separating macromolecules and colloids.

It is a further object of this invention to provide a process for separating macromolecules with higher resolution and versatility than has heretofore existed in the prior art.

It is a still further object of this invention to provide an apparatus for separating macromolecules and colloids which automatically detects and quantifies the separated species.

These as well as other objects are acomplished by carrying out an elution process within an electrical field.

DETAILED DESCRIPTION

Figure 1:
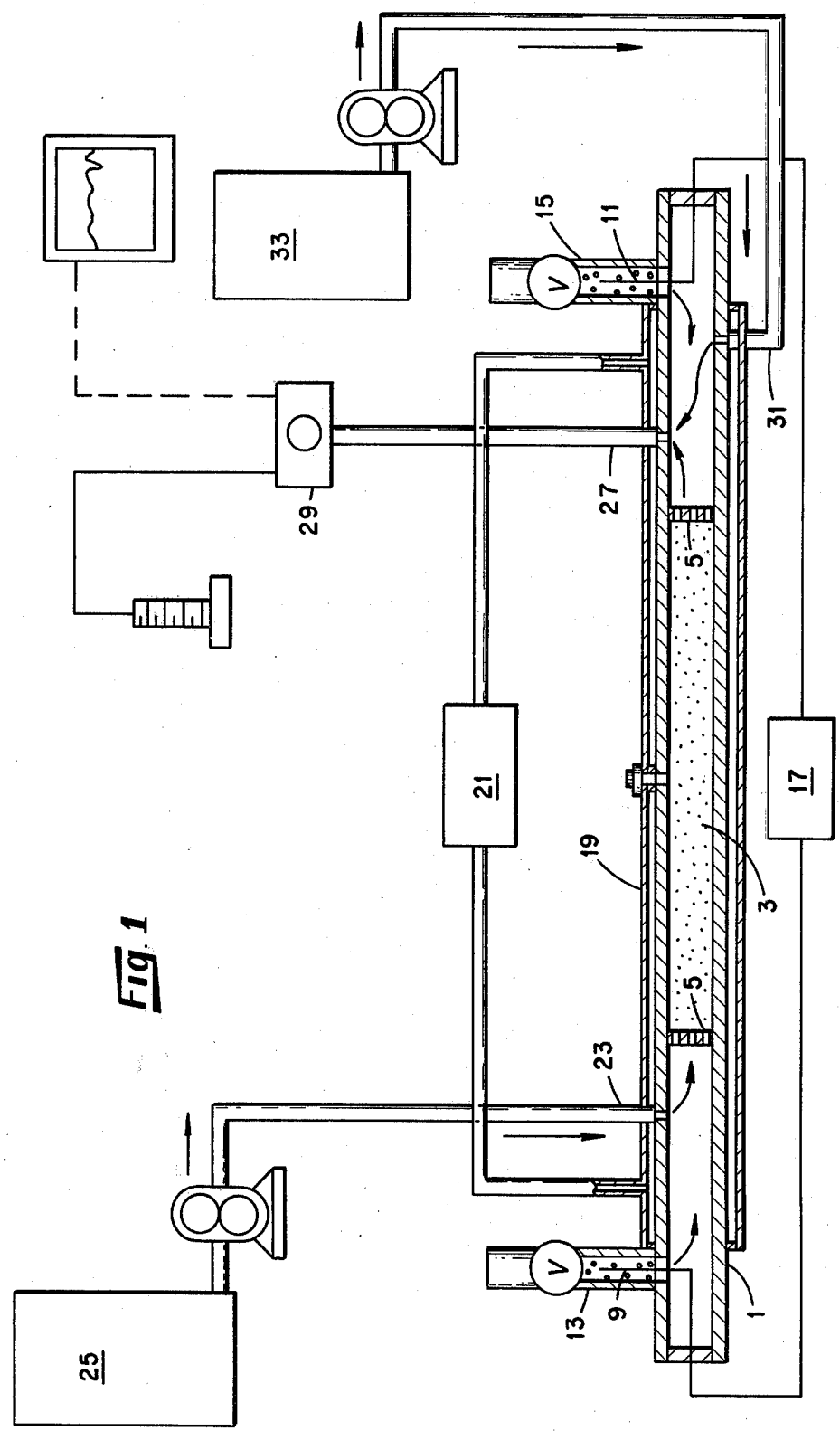
FIG. 1 is a schematic illustration of an apparatus in accordance with this invention.

In accordance with this invention, it has been found that macromolecules can be continuously separated with synergistic results by simultaneously eluting and electrophoretically separating. The process of this invention thus combines the beneficial effects achieved by the prior art processes of gel chromatography and electrophoresis, while substantially eliminating adverse effects which are attributable to either process alone. The process of simultaneously eluting and electrophoretically separating is thus quicker and achieves greater resolution than the prior art processes carried out either separately or consecutively.

As will be more apparent from the detailed description of the apparatus which will follow, the process of this invention comprises introducing a sample containing macromolecules and/or colloidal suspensions to be separated into a central portion of an elongated packed column. Eluent is introduced at one end of the column, which tends to carry the sample through the packing toward the other end of the column. Simultaneously with the step of eluting, an emf is imposed across substantially the entire length of the elongated column. The sample is thus separated into components by the natural movement with the eluent through the packed column and also by the imposed emf which tends to separate particles based upon their charge and mass differences.

The column used in carrying out this invention is packed with conventional separation or anticonvective media such as those used in gel chromatography. The separation media or packing must have sufficient porosity and/or particle size to allow the eluting stream to pass through the column. The packing must also be essentially non-conducting and non-interacting with the species being separated. The principal function of the packing is to prevent convective mixing as the electrophoretic process is carried out. However, chromatographic properties of the packing may also be used to achieve further resolution.

The eluent used in carrying out the process of this invention is the same buffer solution as would be selected for use in conventional electrophoresis. It must be essentially non-interacting with the species being separated, while also having sufficient buffering action to maintain a constant pH.

An essential aspect of this invention is the application of a direct current voltage across the column. Ideally the voltage should be as high as possible. However, the voltage must be limited so as to prevent significant temperature gradiants within the electrophoretic medium. Since the speed of separation is almost linearly dependent on the voltage, the voltage is preferably as high as possible without creating a gradient or raising the column temperature to the point of affecting adversely any of the sample species. The polarity of the field has not been found to be a major factor in the process. The process is operable with a polarity in either direction. Some sample systems, however, may respond to a particular polarity better than others.

The apparatus in accordance with this invention is illustrated in FIG. 1 and comprises a column 1 with a porous packing 3 held in place by porous frit membrane 5. The column 1 has a sample introduction port 7 within a central portion of the column. The port 7 is preferably at the center of the column but it may be at essentially any point as long as the sample travels a sufficient distance for separation to occur, e.g. 10 cm. Electrodes 9 and 11 are positioned within their own chambers 13 and 15 such that bubble formation due to electrolysis does not interfere with the actual operation of the column. By the electrode arrangement as depicted in accordance with this invention, bubbles produced by electrolysis are merely vented through the top of chambers 13 and 15. Electrolysis gases can be vented either at ambient pressure or at elevated pressure. Chambers 13 and 15 may also be closed by the designated valves to increase the column pressure. Electrodes 9 and 11 are connected to an appropriate D.C. power source 17. Substantially all of column 1 is temperature controlled by water jacket 19 communicating with appropriate temperature control means 21. Eluent enters column 1 at port 23 from an eluent source 25. Sample and eluent are removed from column 1 at extraction port 27 which communicates with detection means 29 such as a photometer or colorimeter. The detection means 29 preferably also includes means for introducing reagents into the eluate stream for use in detection by reagent development techniques. Sample losses into downstream electrode chamber 15 are prevented by flow balancing means 31 communicating with an eluent source 33. By controlling the flow of eluent through port 31, substantially the entire volume of sample and eluent passing through column 1 can be diverted through extraction port 27.

The two eluent sources 23 and 31 provide sweeping flows away from each electrode chamber thus preventing accumulation of the separated species in the electrode chambers. The sweeping flows from the sources 23 and 31 must be greater than the electrophoretic migration to prevent this accumulation. The sweeping flows also prevent electrolysis gas from reaching the separation part of column 1.

While not readily apparent from the above description, a great and unexpected advantage which is achieved by the process and apparatus of this invention is the number of and proximity of samples which may be run on a single column. The column may be operated almost continuously with samples being introduced substantially one after the other with only a pause between samples sufficient for the first sample to clear the introduction port.

Having generally described the method and apparatus of this invention, the following specific examples are given as a further illustration thereof.

EXAMPLE I

Figure 2:
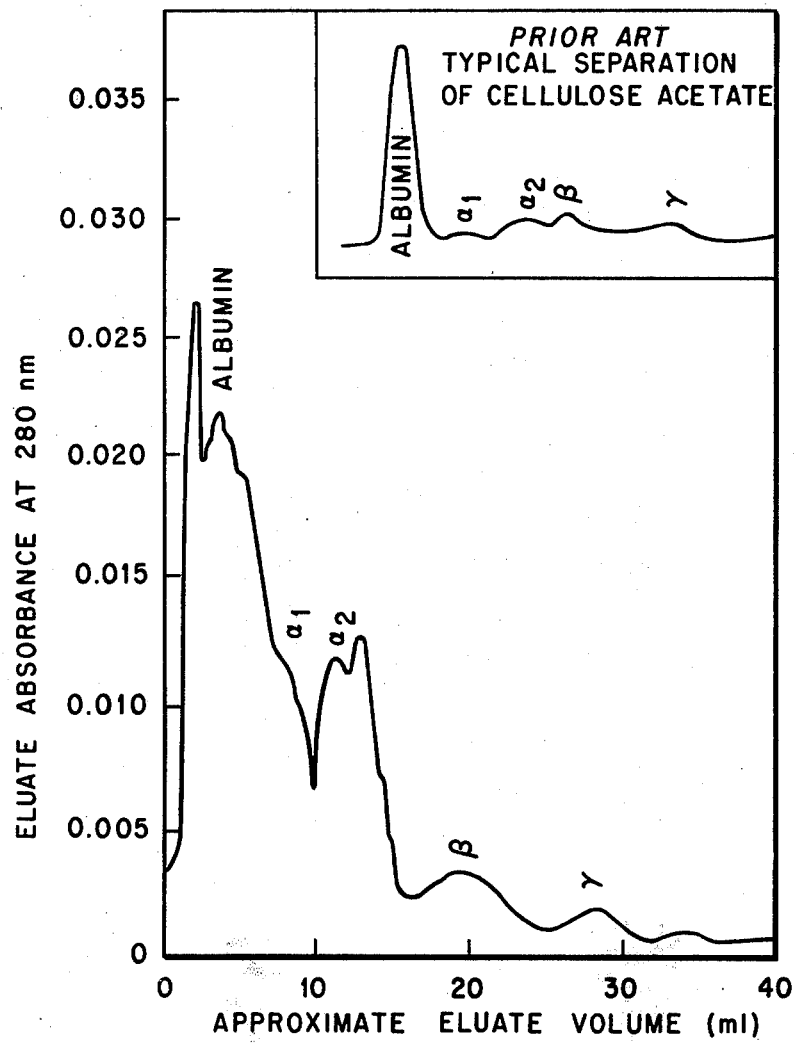
FIGS. 2 and 3 are graphical representations of results achieved in accordance with this invention, along with a comparison of results achieved by prior art techniques.

In the present example, the horizontally disposed column 1 was a 0.3 cm inside diameter × 20 cm long glass tube. An electrical potential of 300 to 1200 volts was applied between the electrodes by a conventional D.C. power source. A positive displacement pump of the dual channel peristaltic type was used to pump the eluent. A highly sensitive flow-monitoring type UV photometer, described in L. H. Thacker et al, J. Chromatography 51, 175 (1970), operating at 254 and 280 nm, was used to detect the separated eluted species. The apparatus utilized a column packing of 200–400 mesh polyacrylamide beads, Bio-Gel, P-2, Bio-Rad Laboratories. Blood serum proteins were separated with a high degree of resolution by the process which follows. The eluent flow was operated at 10 ml per hour. The downstream eluate sweep flow was also operated at 10 ml per hour. An aqueous solution of 0.125 molar sodium phosphate buffered to a pH of 8.6 was used as the eluent. The electrode chambers were closed so that electrolysis gas evolution provided additional flow of both eluent and eluate of about 7 ml/hr. Seven microliters of a pooled serum was introduced by a microsyringe and needle into the sample introduction port in the center of the column. The emf across the column was 1200 V, and temperature was maintained at 3° to 5°C. Detection of the eluate components began in about 10 minutes after introduction. During the course of a one hour run 12 electrophoretic peaks were indicated. These peaks were of the classical pattern of a large albumin peak, followed by smaller $\alpha$, $\alpha_2$, $\beta$ and $\gamma$ globulin peaks as depicted in FIG. 2. Also shown in FIG. 2 are lower resolution results achieved by the prior art technique of electrophoretic separation on a strip of cellulose acetate at a voltage of 200 V. The prior art technique required one to two hours plus additional time for quantitation.

EXAMPLE II

Figure 3:
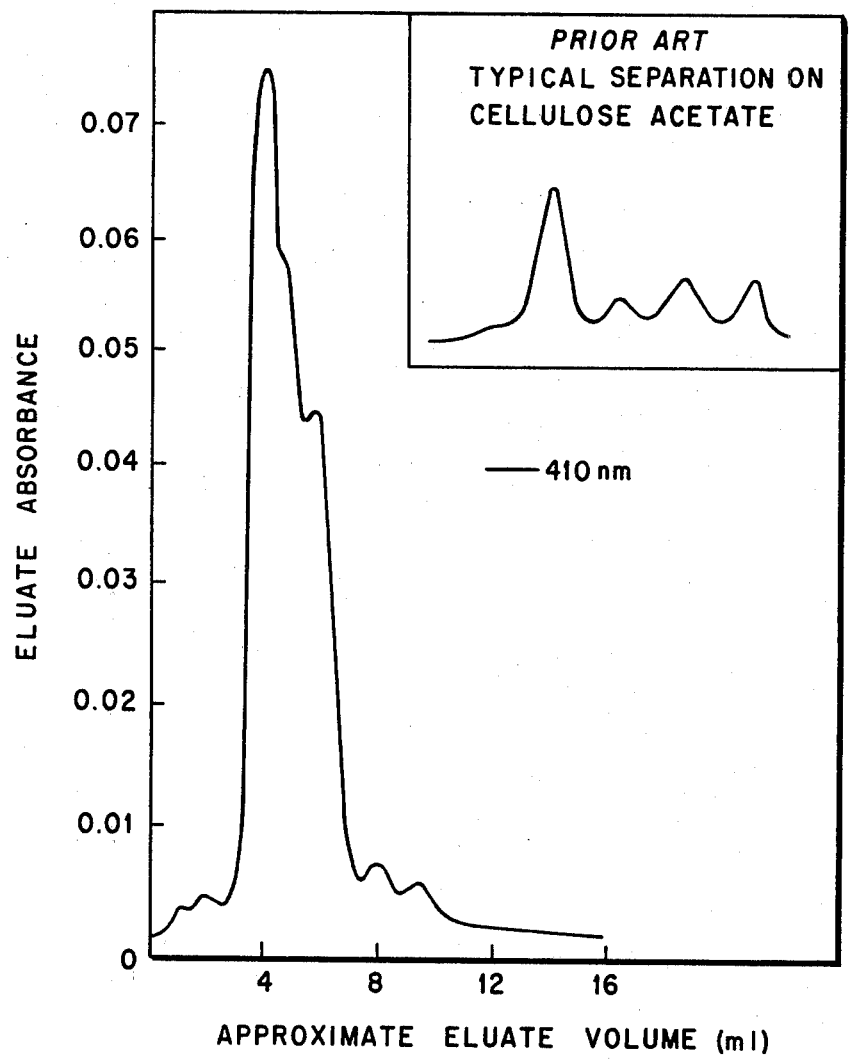

A hemolysate from red blood cells prepared by alternate salination and osmotic rupture in distilled water was used in electrophoretic separation of hemoglobin molecules. One microliter of the hemolysate was introduced into the sample introduction port of the column, using the flow rates and eluent described in Example I. A flow colorimeter operating at 410 nm was used to monitor the eluate. During a one-hour period, five electrophoretic peaks were detected as shown in FIG. 3. For comparison purposes a chromotogram produced by the above-described prior art technique is also shown.

What is claimed is:

1. An apparatus for separating macromolecules, comprising:
   a column packed with a particulate anticonvective medium;
   sample introduction means communicating with a central portion of said column;
   electrode means for applying an emf across the length of said column and positioned adjacent the extremities of said column;
   eluent introduction means at one end of said column;
   eluate extraction means at the other end of said column;

flow balancing means positioned downstream from said eluate extraction means for preventing samples from flowing past said eluate extraction means;

an eluent source communicating with said balancing means; and means for detecting separated molecules communicating with said extraction means.

2. The apparatus according to claim 1 further including a water jacket substantially surrounding the packed section of said column and temperature control means communicating with said jacket.

3. The apparatus according to claim 1 wherein said electrode means are positioned within electrode chambers for permitting electrolysis gases to escape without entering said column.

* * * * *